United States Patent
Bartel et al.

(10) Patent No.: US 9,377,452 B2
(45) Date of Patent: Jun. 28, 2016

(54) METHOD FOR MONITORING THE USE OF A CONSUMABLE IN A DISPOSABLE DESIGN IN ONE OR MORE ANALYZERS

(75) Inventors: Arnold Bartel, Graz (AT); Robert Felsberger, Graz (AT); Horst Ruether, Hart bei Graz (AT); Wolf-Dietrich Steinboeck, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 706 days.

(21) Appl. No.: 12/270,126

(22) Filed: Nov. 13, 2008

(65) Prior Publication Data

US 2009/0151479 A1    Jun. 18, 2009

Related U.S. Application Data

(60) Provisional application No. 60/987,442, filed on Nov. 13, 2007.

(51) Int. Cl.
*G01N 37/00*     (2006.01)
*G01N 33/487*    (2006.01)
*G06F 19/00*     (2011.01)

(52) U.S. Cl.
CPC ........ *G01N 33/48771* (2013.01); *G06F 19/327* (2013.01)

(58) Field of Classification Search
CPC .............................................. G01N 33/48771
USPC ........................................................ 702/84
See application file for complete search history.

(56) References Cited

U.S. PATENT DOCUMENTS 3,504,376 A * 3/1970 Reid ....................... B01L 3/502
                                                       422/561
4,043,756 A * 8/1977 Sommervold ... G01N 35/00693
                                                        422/64

(Continued)

FOREIGN PATENT DOCUMENTS

DE         20113153 U1    3/2002
EP         1739538 A2     1/2007

(Continued)

OTHER PUBLICATIONS

Office Action dated May 15, 2013 pertaining to U.S. Appl. No. 12/713,285, filed Feb. 26, 2010.

(Continued)

*Primary Examiner* — Hyun Park
(74) *Attorney, Agent, or Firm* — Dinsmore & Shohl LLP

(57) ABSTRACT

A method for monitoring the use of a consumable in a disposable design in multiple analyzers is disclosed. The method provides a disposable consumable; uses the consumable as intended during operation of the first analyzer; and collects usage-relevant information for the consumable concerning the intended use of the consumable during operation of the first analyzer. Usage-relevant data derived from the usage-relevant information is stored in a memory unit assigned to the consumable. The consumable may be removed and again provided in the first or second analyzer. The first or second analyzer partially reads the usage-relevant data from the memory unit, evaluates the usage-relevant data, and derives control signals concerning the permissibility and/or type of a further intended use of the consumable during operation of the analyzer as a reaction to the evaluation of the read usage-relevant data.

21 Claims, 2 Drawing Sheets

(56) References Cited

U.S. PATENT DOCUMENTS

| | | |
|---|---|---|
| 6,961,617 B1 | 11/2005 | Snell |
| 7,964,147 B2 | 6/2011 | Schulat et al. |
| 2001/0051952 A1 | 12/2001 | Nakazato |
| 2002/0023198 A1 | 2/2002 | Kokubun et al. |
| 2002/0023852 A1* | 2/2002 | Mcivor .............. A61B 5/14532 206/305 |
| 2003/0126494 A1 | 7/2003 | Strasser |
| 2005/0019213 A1 | 1/2005 | Kechagia et al. |
| 2005/0189219 A1* | 9/2005 | Amirkhanian ....... G01N 21/645 204/403.01 |
| 2005/0236273 A1* | 10/2005 | Han ...................... G01N 27/42 205/81 |
| 2006/0041450 A1 | 2/2006 | Dugan |
| 2006/0148463 A1 | 7/2006 | Zhu et al. |
| 2006/0271607 A1 | 11/2006 | Yawata |
| 2006/0294420 A1 | 12/2006 | Schneider |
| 2007/0265884 A1 | 11/2007 | Lubell et al. |
| 2007/0271316 A1 | 11/2007 | Hollebeek |
| 2008/0015905 A1 | 1/2008 | Lubell et al. |
| 2008/0086609 A1 | 4/2008 | Lesser et al. |
| 2008/0099680 A1 | 5/2008 | Bauer et al. |
| 2008/0117447 A1 | 5/2008 | Okada et al. |
| 2008/0145277 A1 | 6/2008 | Wohland |
| 2008/0146922 A1 | 6/2008 | Steins et al. |
| 2008/0243959 A1 | 10/2008 | Bacastow et al. |
| 2008/0262776 A1 | 10/2008 | Yamasaki et al. |
| 2008/0309481 A1 | 12/2008 | Tanaka et al. |
| 2009/0151479 A1 | 6/2009 | Bartel et al. |
| 2009/0281836 A1 | 11/2009 | Velarde |
| 2010/0037092 A1 | 2/2010 | Zamora |

FOREIGN PATENT DOCUMENTS

| | | |
|---|---|---|
| JP | 2002-162213 | 6/2002 |
| JP | 2003-085423 | 3/2003 |
| JP | 2005-274469 | 10/2005 |
| WO | 03/082091 A2 | 10/2003 |
| WO | 2004/052195 A1 | 6/2004 |
| WO | 2005/040793 A1 | 5/2005 |
| WO | 2008134738 A1 | 11/2008 |
| WO | 2009-062722 A1 | 5/2009 |

OTHER PUBLICATIONS

Office Action pertaining to Japanese Appln. No. 2010-533496.

* cited by examiner

METHOD FOR MONITORING THE USE OF A CONSUMABLE IN A DISPOSABLE DESIGN IN ONE OR MORE ANALYZERS

BACKGROUND OF THE INVENTION

The invention concerns a method for monitoring the use of a consumable in a disposable design in one or more analyzers which are each configured to analyze one or more liquids in particular body fluids.

Medical diagnostic analyzers are known for different analytical purposes. Such analyzers for example include analyzers for analyzing a body fluid. Such an analyzer can for example be a blood gas analyzer. Blood gas analyzers are for example provided as analyzers for determining diagnostically relevant parameters namely the blood gas values, the electrolyte values, the metabolite values, the haematocrit value, haemoglobin parameters and/or bilirubin value of blood samples. They are used in particular for the decentral determination of the aforementioned parameters in whole blood samples. However, applications in veterinary medicine and the use of serum, plasma, urine and dialysate samples are also possible.

Consumables are also regularly used to operate analyzers. Such consumables for example include a so-called sensor cassette which contains the sensors required for an analyte determination. Consumables are furthermore liquid containers or reagent packs which contain the functional fluids such as calibration solutions, washing solutions, reference liquids or reagent solutions required to operate the analyzer. Often several such liquid containers or reagent packs are also combined into so-called fluid packs. A consumable for an automated quality control can also be provided for example in the form of a cassette with reference solutions in ampoules. However, paper for example in the form of a paper cassette or roll for an internal printer may also be one of the consumables in such a medical diagnostic analyzer. A common feature of the aforementioned consumables is that they are consumables in a so-called disposable design, i.e., disposable consumables which are consumed during operation in one or even several analyzers and cannot be regenerated or refilled. In particular, the disposable consumables also include all disposable consumables whose contents are not consumed in a single step, for example in the case of an analytical test strip, but rather are only partially and successively consumed during operation and can therefore be used to carry out a plurality of measurements and associated actions such as calibration, washing steps or such like in one analyzer or successively in several analyzers. Such consumables, that are also referred to as multi-use consumables and can, together with the respective consumable, be used to successively carry out several actions such as measuring cycles, calibration cycles, quality control cycles, cleaning cycles and/or standby phases in which always only a portion of the contents of the consumable is consumed. Such multi-use consumables are frequently in the form of cassettes or fluid packs which are designed for a plurality of measurements or actions associated therewith and can be disposed of in their entirety as disposable consumables for example after they have been completely used up (for example, complete emptying) or after reaching a maximum period of use.

In contrast to this, consumables are known which are reprocessed after use in order to then use them again. These are then consumables in a reusable design. In this connection a multiple reprocessing after prior use may be scheduled at regular intervals so that several cycles of use can be run through after a prior reprocessing in each case. Thus, the reprocessing of microfluidic devices, so-called microchips, is described in the document US 2005/0019213 A1. It is proposed that the microfluidic devices are provided with a data storage module in order to document in particular the number of so-called washing cycles and cycles of use. This for example allows one to determine whether a microfluidic device has already reached or even exceeded a specified maximum number of cycles of use or a specified maximum number of reprocessing cycles.

SUMMARY OF THE INVENTION

It is against the above background that the present invention provides certain unobvious advantages and advancements over the prior art. In particular, the inventors have recognized a need for improvements in methods for monitoring the use of consumables in a disposable design in one or more analyzers.

Although the present invention is not limited to specific advantages or functionality, it is noted that the present invention provides a method for monitoring the use of a consumable in a disposable design in one or more analyzers which are each configured to analyze one or more liquids, in particular body fluids, which enables specifications about use in relation to the disposable consumable to be adhered to. Furthermore, the safety requirements that apply in connection with analyzers are also addressed.

In accordance with one embodiment of the present invention, a method for monitoring the use of a consumable in a disposable design in one or more analyzers which are each configured to analyze one or more liquids, in particular body fluids, is provided where the method comprises the following steps:

providing a disposable consumable in a first analyzer,
using the disposable consumable as intended during operation of the first analyzer,
collecting usage-relevant information for the disposable consumable which concern the intended use of the disposable consumable during operation of the first analyzer,
storing usage-relevant data which are derived from the usage-relevant information in a memory unit assigned to the disposable consumable,
removing the disposable consumable from the first analyzer,
again providing the disposable consumable in the first analyzer or in a second analyzer,
at least partially reading the usage-relevant data from the memory unit in the first or the second analyzer,
evaluating the usage-relevant data that have been read out by a control device, and
deriving control signals concerning the permissibility and/or type of a further intended use of the disposable consumable during operation of the first or of the second analyzer as a reaction to the evaluation of the usage-relevant data that have been read out.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawing, where like structure is indicated with like reference numerals and in which.

Figure 1:
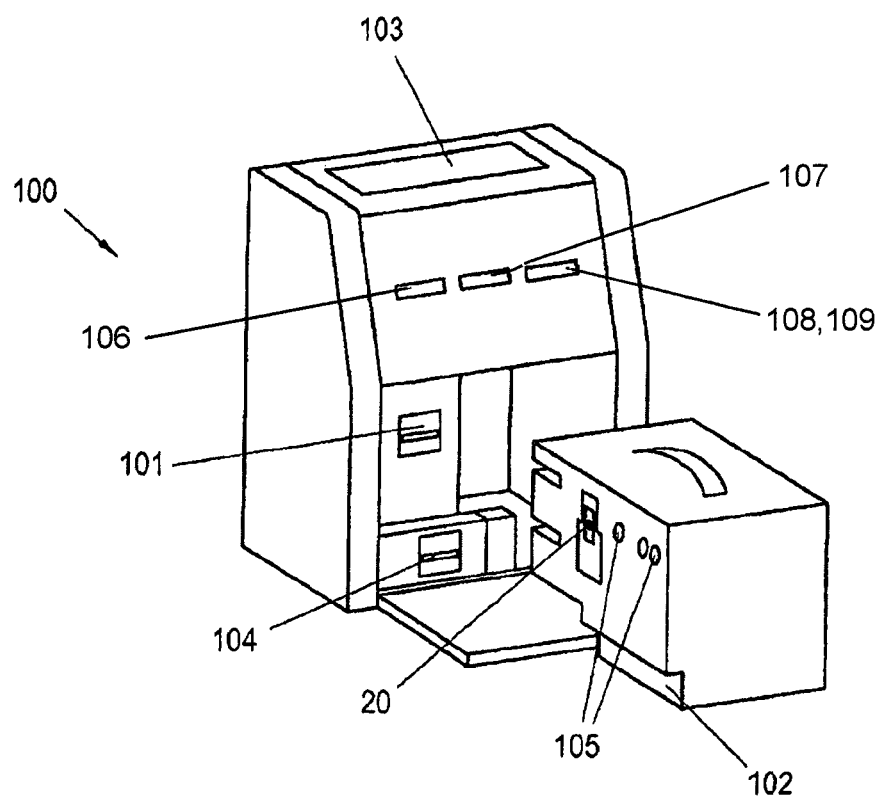
FIG. 1 shows a schematic diagram of an analyzer according to one embodiment of the invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

The invention enables a consumable which has been removed and reinserted in the analyzer once or several times during its life cycle, to be used reliably and as intended. A consumable according to the invention in a disposable design cannot be regenerated and in particular cannot be refilled after it has been manufactured or after it has been completely or partially consumed. It can be used in one or more analyzers which are designed for a plurality of analytical cycles.

The disposable consumables are designed as multi-use consumables, i.e., a plurality of actions can be carried out successively with the aid of the respective consumable such as measuring cycles, calibration cycles, quality control cycles, cleaning cycles and/or standby phases in which only a portion of the contents of the consumable is regularly consumed or utilized. The consumables are thus multi-use consumables in a disposable design which, on the one hand, enable a plurality of measurements and/or associated actions but, on the other hand, are disposed of typically as an entirety in a suitable manner after they have been used or consumed as intended.

The successive usage of such a multi-use disposable consumable in different analyzers or also in the same analyzer is especially expedient when the disposable consumable is used relatively rarely and for example additionally has a limited period of use. This may for example be the case for quality control media which are only used at certain relatively long time intervals or after a certain number of analyte determinations. In this case the usage of the disposable consumables can be optimized by a combined usage of such multi-use consumables on several analytical systems in that for example the maximum possible number of quality control measurements within the period specified by the storage life can be carried out which makes it more economical and reduces waste. Other examples of practical applications of the method are for example expensive sensors for analyte determinations that are seldom carried out which thus only have to be in stock singly or in a few versions since they can be exchanged between different analyzers depending on the intended use and necessity, or sensors which for example respond to elevated temperatures during use in the analyzer with a reduced lifetime and therefore have to be removed from the analyzer after a measurement, stored under better-tolerated environmental conditions and again inserted into the same analyzer or also into a different analyzer for a subsequent measurement.

By collecting and storing usage-relevant data it is possible for each disposable consumable to monitor under which conditions the consumable has been previously used. The usage-relevant data can relate to a wide variety of aspects of the use of the disposable consumable in the operation of one or more analyzers. If after being previously removed from a first analyzer, the disposable consumable is again inserted into this analyzer or into a second analyzer this usage-relevant data filed in the memory unit assigned to the disposable consumable is evaluated in order to establish whether the intended further use by the user can take place at all and in a correct manner. For this purpose appropriate control signals are generated which can then be evaluated for subsequent actions. In this manner a decision is made about the reliability and/or the type of a further intended use. Hence, the control signals constitute electronic information which indicates the decision or decisions with regard to the permissibility and/or type of a further intended use. From this it is then possible to derive any further actions in accordance with the decision, for example an appropriate user information and/or control of the analyzer.

The memory unit in which the usage-relevant data are stored can be directly and permanently, detachably or non-detachably mounted on the disposable consumable. For example it is possible to use an electronic memory module which can be a memory chip or an RFID chip. The memory unit typically has a non-volatile memory.

In a typical embodiment of the method the derivation of the control signals can comprise the following steps: generating control signals by a control device as a reaction to the evaluation of the usage-relevant data that have been read out where the control signals indicate the permissibility of a further intended use of the disposable consumable when in the evaluation of the usage-relevant data that have been read out, it is established that the further intended use of the disposable consumable is allowable during operation of the first or the second analyzer, and the control signals indicate the further intended use of the disposable consumable is not permissible when in the evaluation of the usage-relevant data that has been read out it is established that the further intended use of the disposable consumable is impermissible during the operation of the first or the second analyzer.

A typical further development of the invention envisages that the following steps are additionally provided when the control signals indicate the permissibility of the further intended use of the disposable consumable: further intended use of the disposable consumable during the operation of the first or the second analyzer, collecting further usage-relevant data which relate to the further intended use of the disposable consumable during the operation of the first or the second analyzer and storage of additional usage-relevant data which are derived from the additional consumable-relevant information in the memory unit assigned to the disposable consumable. Hence, if the control signals indicate the permissibility of a further intended use of the disposable consumable, it is further used in an identical manner or a manner modified due to the previous usage which is then in turn monitored for example with the aid of a monitoring device located in the analyzer such that additional usage-relevant information are collected and data derived therefrom are stored. A further usage modified on the basis of the previous usage of the consumable can for example in the case of a sensor cassette as a disposable consumable mean that after a conditioning process such as for example a so-called wet-up phase has been carried out once for dry-stored electrochemical sensors when the sensor cassette is used for the first time, it is not compulsory to carry out this conditioning process when the same sensor cassette is subsequently inserted again into the same analyzer or into another analyzer. The further usage-relevant data can be stored as an addition to the already existing data in the memory unit so that a complete history of all these usage-relevant data is present on the memory element. The originally stored data can also be partially replaced by the subsequent usage-relevant data by at least partially updating and overwriting existing usage-relevant data.

In a typical embodiment of the invention it is provided that data influencing the type of further intended use of the disposable consumable are derived from the usage-relevant data that have been read out. On the basis of the derived data, the further intended use of the disposable consumable in the first or the second analyzer is then controlled. For example characteristic data of reference materials, for example target concentrations of substances contained in the reference materials which are used during the further intended use of the disposable consumable in the analyzer, can be re-adjusted on the basis of the stored usage-relevant data. If in such an embodiment it is for example deduced from the usage-relevant data that have been read out that the disposable consumable (in this case the reference materials) has been subjected to a certain temperature stress during an earlier intended use, temperature dependent parameters of the reference material can be readjusted for the further intended use of the disposable consumable. Thus, a temperature stress previously experienced by the disposable consumable which is for example characterized by a certain temperature over a determined time period, can lead to a percentage adjustment of one or more temperature-dependent parameters of the reference material. This can for example be applied in connection with organic reference substances such as glucose or urea which are degraded at an accelerated rate at elevated temperatures and thus corresponding changes in the target concentrations of these reference substances occur.

In a further advantageous embodiment of the invention it can be provided that a user information indicating the inadmissibility of the further intended use of the disposable consumable is generated when the control signals indicate the inadmissibility of the further intended use of the disposable consumable. The user information can optionally encompass an acoustic and/or an optical signal for the user. If the analyzer has a display, it is for example possible to display on it an appropriate text message for the user. Such a display for example draws the user's attention to the fact that further operation of the analyzer with this particular disposable consumable must cease.

An advantageous embodiment of the invention provides that the further intended use of the disposable consumable in the first or the second analyzer is prevented when the control signals indicate the inadmissibility of the further intended use of the disposable consumable. In this embodiment the control signals interpret the inadmissibility to mean that further use of the disposable consumable is prevented. In one embodiment the user can be additionally informed about this by means of a suitable signalling, for example with the aid of an acoustic and/or optical signal.

A further development of the invention provides that the collected usage-relevant information and the collected usage-relevant information comprises one or more information aspects selected from the following group of information aspects:
  one or more conditions of use for the intended use or for the further intended use of the disposable consumable such as chemical usage parameters and/or physical usage parameters,
  a period of use for the intended use or for the further intended use of the disposable consumable or the period the disposable consumable stays outside the analyzer after it has been removed from the first analyzer,
  time at which the disposable consumable is inserted into the first or the second analyzer,
  period of non-use of the disposable consumable after it has been removed from the first analyzer,
  actions carried out with the aid of the disposable consumable such as measuring cycles, calibration cycles, quality control cycles, cleaning cycles and/or standby phases, and
  amount consumed and/or extent of consumption of the disposable consumable during its intended use and/or during its further intended use such as the number of consumed ampoules or the number and/or amount of consumed reagents.

The period of non-use of the disposable consumable after being removed from the analyzer relates to the period outside an analyzer. If as an information aspect the amount consumed and/or the extent of consumption of the disposable consumable are affected, it is for example possible to register a removal of aliquots of the contents of the disposable consumable.

Suitable usage parameters include in general all parameters which can yield information about the conditions or manner of use of the respective disposable consumable which can have an effect on the subsequent intended use of the respective consumable in this analyzer or also in another analyzer. Such usage parameters can typically be physical or chemical parameters and values derived therefrom.

The physical usage parameters for example include information about the temperature to which the disposable consumable has been exposed during operation of the analyzer. Another possible physical usage parameter is for example the air humidity which can have a disadvantageous effect on certain properties such as the storage stability of the disposable consumable. Also information about temperature-dependent substance concentrations and time-dependent concentration changes can be registered and stored for the disposable consumable. In this manner it is for example possible to document a temperature stress during use of the disposable consumable. This means it is for example possible to calculate decay rates of analytes in reference materials and thus re-adjust characteristic data of reference materials. Furthermore, conclusions may be made therefrom about whether the consumable has perhaps been damaged due to an excessive temperature stress and can thus no longer be used.

A chemical usage parameter is for example a usage-specific analyte content of a liquid contained in the consumables, for example the oxygen partial pressure or the oxygen concentration of a certain functional fluid, which can be determined with the aid of a suitable sensor used by the monitoring device. This allows the determination of a qualitative and/or quantitative change of further ingredients of the disposable consumable such as an associated, for example oxidative degradation of organic ingredients, in order to on this basis set or readjust reference values for the further process of use during the intended use of the disposable consumable in the analyzer. In a similar manner this readjustment can also be provided in connection with sensors which detect other chemical or physical parameters of the disposable consumable. In the case of a sensor cassette comprising one or more biosensors, a decrease in the activity of enzymes contained in the biosensors as a result of the number of measurements that have already been carried out therewith as well as of the respective analyte concentrations of the measured liquid samples can for example be detected.

In an advantageous embodiment of the invention it can be provided that when collecting usage-relevant information and/or when collecting further usage-relevant information, partial information is collected at time intervals. In this manner it is for example possible to regularly or randomly collect the usage-relevant information during the use of the disposable consumable.

A further development of the invention can provide that the collection of usage-relevant information and/or the collection of further usage-relevant information takes place in each case before, during and/or after the intended use or the further intended use of the disposable consumable.

A typical further development of the invention provides that partial data are stored at intervals when storing usage-relevant data and/or storing further usage-relevant data.

An advantageous embodiment of the invention can provide that the usage-relevant data are stored in the assigned memory unit before the disposable consumable is removed from the first analyzer and/or the further usage-relevant data are stored before the disposable consumable is removed from the first or the second analyzer. This ensures that at least at this time all usage-relevant information that are necessary for a possible further use of the disposable consumable are stored on the memory element assigned to this disposable consumable and can thus be passed on to the first or also to another analyzer together with the disposable consumable when this consumable is subsequently used in the first or another analyzer.

In an advantageous embodiment of the invention it can be provided that after the disposable consumable has been provided in the first or the second analyzer, data that are independent of the usage or consumption of the disposable consumable continue to be read out. Data that are independent of the usage or consumption of the disposable consumable can for example comprise the production date, an expiry date or batch-specific information. It can also be provided that the data that are independent of the consumption of the disposable consumable comprise information about in which types of analytical instruments the respective disposable consumable can be used. When the disposable consumable is inserted into the analyzer, the data that are independent of the usage or consumption can be completely or partially evaluated in order to on this basis and possibly also in combination with usage-relevant data, for example release or block its use in the analyzer.

In an advantageous embodiment of the invention it can be provided that the usage-relevant information and/or the further usage-relevant information for the disposable consumable is collected with the aid of a monitoring device of the first/second analyzer. The monitoring device of the respective analyzer is configured to collect the usage-relevant information and/or the further usage-relevant information for the disposable consumable by for example providing a sensory system adapted to the information to be collected.

A further development of the invention can provide that the storage of usage-relevant data and/or the storage of further usage-relevant data in the memory unit assigned to the disposable consumable is stored with the aid of a writing device of the first/second analyzer. The writing device of the respective analyzer is configured to write the usage-relevant information and/or the further usage-relevant information into the assigned memory unit using data communication for example with the aid of a wireless data exchange.

A typical further development of the invention provides that the usage-relevant data are at least partially read from the memory unit with the aid of a reading device of the first/second analyzer. The reading device of the respective analyzer is configured to read the usage-relevant information from the assigned memory unit using data communication for example with the aid of a wireless data exchange.

FIG. 1 shows a schematic diagram of an analyzer 100 which is an analyzer for determining a body fluid, for example a blood gas analyzer. This analyzer 100 is designed to be "virtually maintenance free" so that all consumables required for routine operation are present as disposable consumables in the form of cassettes and/or modules which are also referred to as consumables and therefore can also be replaced by (technically) untrained personnel. In this embodiment example the materials and consumables that are used are combined in the following disposable consumables:

A sensor cassette 101 which contains at least some and typically all sensors required for the analyte determination.

A fluid pack 102 which contains liquid and waste containers which contain the operating or functional liquids required to operate the analyzer 100 such as, for example, calibration or reference liquids, washing and cleaning liquids or also reagent liquids. Further elements or functionalities such as the entire fluidic system or parts thereof such as the sample input device or also further sensory components may optionally be present in the fluid pack 102.

A printer paper cassette 103 for an internal printer.

Optionally a quality control cassette 104 containing reference solutions in the form of ampoules for carrying out an automated quality control which the personnel can replace themselves by simple intuitive manual steps.

The subdivision of the disposable consumables described here is only an example. It can also be envisaged that (partial) functionalities or (partial) elements of several disposable consumables are combined so that for example fewer disposable consumables or even only one disposable consumable is required. On the other hand, it is also conceivable that (partial) functionalities or (partial) elements of individual disposable consumables are distributed for example among several sensor cassettes or modules.

The disposable consumables are coupled together or to the analyzer 100 by means of compatible interfaces for example in the form of fluidic docking nipples 105 or electrical contacts (not shown). The disposable consumables can be mechanically connected to their respective counterparts either directly by the user with the aid of a simple manual sequence of movements or with the aid of drives located in the device which automatically carry out the coupling after the user has only brought the cassette into "position".

For example a sensor cassette 101 can be inserted as a disposable consumable into an assigned opening of the analyzer 100 and removed therefrom. In a similar manner the fluid pack 102 can be inserted into or removed from an assigned holder of the analyzer 100.

The liquid container 102 contains the functional liquids necessary for the operation of the analyzer 100, for example in the form of ampoules or other containers which can dispense partial volumes of the liquids contained therein into the analyzer 100 or other disposable consumables. When the liquid container 102 is inserted, it is coupled to the analyzer 100 for example by means of fluidic docking nipples 105. After the various disposable consumables have been inserted, they are typically mechanically locked into the analyzer 100 in order to prevent them from accidentally falling out or being removed.

If only one of the aforementioned disposable consumables 101, 102, 103 or 104 is inserted into the analyzer 100, an electronic memory module 20 is read out, said module being arranged on the respective disposable consumable such as on the fluid pack 102 in the case shown. The electronic memory module 20 is for example a memory chip or an RFID chip. For this purpose the analyzer 100 has allocated writing/reading means (not shown) which are configured to write electronic data into the electronic memory module 20 and to read data therefrom. The data that are read out are evaluated in a control device 106 which for example comprises a microprocessor and an appropriate software program in order to generate control signals that are derived therefrom which indicate whether an intended use of the inserted disposable consumable is permissible or not in the analyzer 100. For this purpose usage-relevant data from the electronic memory module 20 which contain information about the use of the disposable consumable that has already occurred or has yet to occur, is evaluated.

Depending on the usage-relevant data of the memory module 20 that are read out after the disposable consumable has been inserted, it may be arranged that operating parameters are set for the use of the disposable consumable, for example a maximum temperature stress. Also when the disposable consumable is used to make a determination in the liquid to be analyzed, it is also for example possible to set operating parameters for the reference materials that are used in this connection which are derived from the usage-relevant data that are read out.

If after insertion into the analyzer 100, the disposable consumable 101, 102, 103 or 104 is used as intended, electronic data concerning this intended use are subsequently written into the electronic memory module 20. In order to generate such electronic data, the analyzer 100 has suitable monitoring means/device 107 for collecting usage-relevant information, for example in the form of a temperature sensor, a clock and/or a counting unit.

The temperature sensor can for example be used to register an ambient temperature during the operation of the analyzer 100 in order to document which temperatures the respective disposable consumable has been exposed to during use. In this case a temperature curve detected continuously or at intervals can for example be registered as usage-relevant information. Usage-relevant data can then be derived therefrom for example by means of suitable evaluation methods such as accumulated or averaged temperature stress or the number of times and/or the period of certain predetermined temperature limits have been exceeded or undercut.

A clock can for example be used to register the times at which a disposable consumable has been inserted into or removed from the analyzer 100 (in the sense of a spot time measurement) or to register the period the disposable consumable has been in the analyzer 100 (in the sense of a stop watch measurement) as usage-relevant information from which usage-relevant data can be derived by suitable evaluation methods, for example the period of use in the analyzer from the spot time measurements or alternatively the period the disposable consumable has remained outside an analyzer after being removed from the first analyzer.

Similarly additional usage-relevant information can also be registered by a clock during operation and use, for example the start and end of actions involving the disposable consumable such as measuring cycles, calibration cycles, quality control cycles, cleaning cycles and/or standby phases or their duration. Additional usage-relevant data can be derived therefrom with the aid of suitable evaluation methods, for example a cumulated period during which a sensor has been exposed to certain functional liquids, such as cleaning solutions or calibration solutions which may have effects on its subsequent use and in particular on the maximum period of use of the sensor.

The counting unit can for example be used to register the number of actions involving the disposable consumable in the analyzer that have already occurred, or by counting backwards, the number of actions that are still possible such as measuring cycles, calibration cycles, quality control cycles, cleaning cycles and/or standby phases as additional usage-relevant information from which additional usage-relevant data can be derived by suitable evaluation methods such as time data when the duration of such an action/cycle is known, for example the cumulated period of time during which a certain sensor has been exposed to certain functional liquids such as cleaning solutions or calibration solutions which may have effects on its subsequent use and in particular on the maximum period of use of the sensor.

If the disposable consumable is removed from the analyzer 100 after use, these usage-relevant data stored in the electronic memory module 20 are available to this same analyzer or also to another analyzer for an evaluation when it is reinserted into the same analyzer or into another analyzer. In this manner it is possible to register and document the conditions of use over the lifecycle of the disposable consumable. In particular in this manner it is possible to prevent a disposable consumable from still being used even when conditions of use have occurred during a previous use which probably or certainly have damaged the disposable consumable. The usage-relevant data stored in the electronic memory module 20 give information about this.

Figure 2:
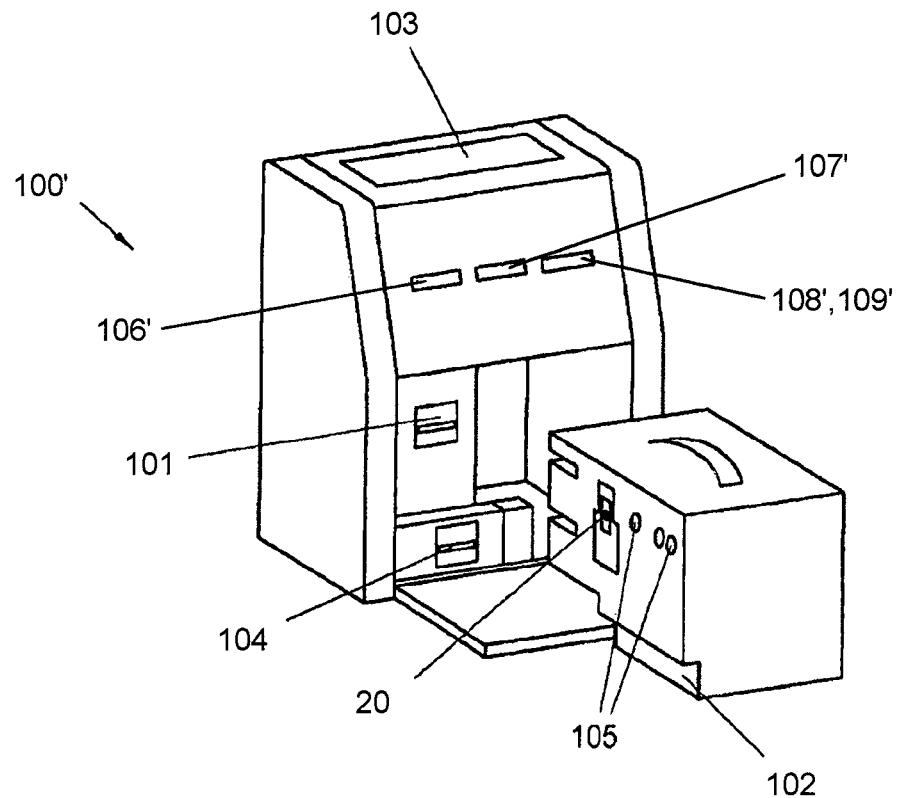
FIG. 2 shows a schematic diagram of another analyzer according to one embodiment of the invention.

In another embodiment, a method for monitoring the use of a consumable in a disposable design in one or more analyzers which are each configured to analyze one or more liquids is disclosed. The method may comprise providing a disposable consumable 101, 102, 103 or 104 in a first analyzer 100, using the disposable consumable 101, 102, 103 or 104 as intended during operation of the first analyzer 100, collecting usage-relevant information for the disposable consumable 101, 102, 103 or 104 which concern the intended use of the disposable consumable 101, 102, 103 or 104 during operation of the first analyzer 100, storing usage-relevant data which are derived from the usage-relevant information in a memory unit 20 assigned to the disposable consumable 101, 102, 103 or 104, removing the disposable consumable 101, 102, 103 or 104 from the first analyzer 100, again providing the disposable consumable 101, 102, 103 or 104 in the first analyzer 100 or in a second analyzer 100' (FIG. 2), at least partially reading the usage-relevant data from the memory unit 20 in the first or the second analyzer 100, 100', evaluating the usage-relevant data that have been read out by a control device 106, 106', and deriving control signals concerning the permissibility and/or type of a further intended use of the disposable consumable during operation of the first or of the second analyzer 100, 100' as a reaction to the evaluation of the usage-relevant data that have been read out.

In another embodiment, when the control signals indicate the permissibility of the continued intended use of the disposable consumable 101, 102, 103 or 104, the method may further comprise continuing the intended use of the disposable consumable 101, 102, 103 or 104 during the operation of the first or the second analyzer 100, 100', collection of further usage-relevant information which concern the further intended use of the disposable consumable 101, 102, 103 or 104 during the operation of the first or the second analyzer 100, 100', and storage of further usage-relevant data which are derived from the further consumable-relevant information in the memory unit assigned to the disposable consumable.

In another embodiment, a method wherein data are derived from the usage-relevant data that are read out which influence the manner in which the disposable consumable is subsequently used as intended.

In another embodiment, a method wherein a user information indicating the inadmissibility of the further intended use of the disposable consumable 101, 102, 103 or 104 is generated when the control signals indicate the inadmissibility of the further intended use of the disposable consumable 101, 102, 103 or 104.

In another embodiment, a method wherein further intended use of the disposable consumable 101, 102, 103 or 104 in the first or the second analyzer 100, 100' is prevented when the control signals indicate the inadmissibility of the further intended use of the disposable consumable 101, 102, 103 or 104.

In another embodiment, a method wherein the collected usage-relevant information and the collected further usage-relevant information comprises one or more information aspects selected from one or more conditions of use for the intended use or further intended use of the disposable consumable 101, 102, 103 or 104 such as chemical usage parameters and/or physical usage parameters, a period of use for the intended use or for the further intended use of the disposable consumable 101, 102, 103 or 104, a period of non-use of the disposable consumable 101, 102, 103 or 104 after it has been removed from the first analyzer 100, a time at which the disposable consumable 101, 102, 103 or 104 is inserted into the first or the second analyzer 100, 100', the actions carried out with the aid of the disposable consumable 101, 102, 103 or 104 such as measuring cycles, calibration cycles, quality control cycles, cleaning cycles and/or standby phases, and the amount consumed and/or extent of consumption of the disposable consumable 101, 102, 103 or 104 during its intended use and/or during its further intended use.

In another embodiment, a method wherein when collecting usage-relevant information and/or when collecting further usage-relevant information, partial information is collected at time intervals.

In another embodiment, a method wherein the collection of usage-relevant information and/or the collection of further usage-relevant information takes place in each case before, during and/or after the intended use or the further intended use of the disposable consumable 101, 102, 103 or 104.

In another embodiment, a method wherein partial data are stored at intervals when storing usage-relevant data and/or storing further usage-relevant data.

In another embodiment, a method wherein the usage-relevant data are stored in the assigned memory unit 20 before the disposable consumable 101, 102, 103 or 104 is removed from the first analyzer 100 and/or the further usage-relevant data are stored in the assigned memory unit 20 before the disposable consumable 101, 102, 103 or 104 is removed from the first or the second analyzer 100, 100'.

In another embodiment, a method wherein after the disposable consumable 101, 102, 103 or 104 has been provided in the first or the second analyzer 100, 100', data that are independent of the usage or consumption of the disposable consumable 101, 102, 103 or 104 continue to be read out.

In another embodiment, a method wherein the usage-relevant information and/or the further usage-relevant information for the disposable consumable 101, 102, 103 or 104 is collected with the aid of a monitoring device 107, 107' of the first/second analyzer 100, 100'.

In another embodiment, a method wherein the storage of usage-relevant data and/or the storage of further usage-relevant data in the memory unit 20 assigned to the disposable consumable 101, 102, 103 or 104 is stored with the aid of a writing device 108, 108' of the first/second analyzer 100, 100'.

In another embodiment a method wherein the usage-relevant data are at least partially read from the memory unit 20 with the aid of a reading device 109, 109' of the first/second analyzer 100, 100'.

In another embodiment, a method wherein the liquid is a body fluid.

It is noted that terms like "preferably", "commonly", and "typically" are not utilized herein to limit the scope of the claimed invention or to imply that certain features are critical, essential, or even important to the structure Or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for monitoring the use of a consumable in a disposable design in multiple analyzers which are each configured to analyze one or more liquids, wherein the consumable is a liquid container or a reagent pack containing one or more functional fluids comprising reference materials having characteristic data and which have target concentrations of substances contained therein which degrade based on usage due to at least one of temperature and time, wherein the method comprises:

providing a disposable consumable in a first analyzer, using the disposable consumable as intended during operation of the first analyzer, collecting usage-relevant information for the disposable consumable which concern the intended use of the disposable consumable during operation of the first analyzer, wherein the collected usage-relevant information comprises information about one or more conditions of use for the intended use or further intended use of the disposable consumable which are chemical usage parameters and/or physical usage parameters, storing usage-relevant data which are derived from the usage-relevant information in a memory unit assigned to the disposable consumable, removing the disposable consumable from the first analyzer, providing the disposable consumable in a second analyzer, at least partially reading the usage-relevant data from the memory unit in the second analyzer, evaluating the usage-relevant data that have been read out by a control device, and deriving control signals concerning the permissibility or type of a further intended use of the disposable consumable during operation of the second analyzer as a reaction to the evaluation of the usage-relevant data that have been read out, and re-adjusting in the second analyzer the characteristic data of the reference materials on the basis of the stored usage-relevant data that have been read out to account for degradation of the target concentrations of substances contained in the reference materials based on the usage in the first analyzer.

2. The method according to claim 1, further comprises, when the control signals indicate the permissibility of the continued intended use of the disposable consumable,
- continuing the intended use of the disposable consumable during the operation of the second analyzer,
- collecting further usage-relevant information which concern the further intended use of the disposable consumable during the operation of the second analyzer, and
- storing of the further usage-relevant data which are derived from the further consumable-relevant information in the memory unit assigned to the disposable consumable.

3. The method according to claim 1, wherein data are derived from the usage-relevant data that are read out which influence the manner in which the disposable consumable is subsequently used as intended.

4. The method according to claim 1, wherein a user information indicating the inadmissibility of the further intended use of the disposable consumable is generated when the control signals indicate the inadmissibility of the further intended use of the disposable consumable.

5. The method according to claim 1, wherein further intended use of the disposable consumable in the second analyzer is prevented when the control signals indicate the inadmissibility of the further intended use of the disposable consumable.

6. The method according to claim 1, wherein the collected usage-relevant information and the collected further usage-relevant information comprises one or more information aspects selected from the following group of information aspects:
- one or more conditions of use for the intended use or further intended use of the disposable consumable such as chemical usage parameters and/or physical usage parameters,
- a period of use for the intended use or for the further intended use of the disposable consumable,
- a period of non-use of the disposable consumable after it has been removed from the first analyzer,
- a time at which the disposable consumable is inserted into the first or the second analyzer,
- the actions carried out with the aid of the disposable consumable such as measuring cycles, calibration cycles, quality control cycles, cleaning cycles and/or standby phases, and
- the amount consumed and/or extent of consumption of the disposable consumable during its intended use and/or during its further intended use.

7. The method according to claim 1, wherein when collecting usage-relevant information or when collecting further usage-relevant information, partial information is collected at time intervals.

8. The method according to claim 1, wherein the collection of usage-relevant information or the collection of further usage-relevant information takes place in each case before, during or after the intended use or the further intended use of the disposable consumable.

9. The method according to claim 1, wherein partial data are stored at intervals when storing usage-relevant data or storing further usage-relevant data.

10. The method according to claim 1, wherein the usage-relevant data are stored in the assigned memory unit before the disposable consumable is removed from the first analyzer or the further usage-relevant data are stored in the assigned memory unit before the disposable consumable is removed from the second analyzer.

11. The method according to claim 1, wherein after the disposable consumable has been provided in the first or the second analyzer, data that are independent of the usage or consumption of the disposable consumable continue to be read out.

12. The method according to claim 1, wherein the usage-relevant information or further usage-relevant information for the disposable consumable is collected with the aid of a monitoring device.

13. The method according to claim 12, wherein the monitoring device is in the form of a temperature sensor, a clock or a counting unit.

14. The method according to claim 1, wherein the storage of usage-relevant data or storage of further usage-relevant data in the memory unit assigned to the disposable consumable is stored with the aid of a writing device.

15. The method according to claim 1, wherein the usage-relevant data are at least partially read from the memory unit with the aid of a reading device.

16. The method according to claim 1, wherein the liquid is a body fluid.

17. The method according to claim 1, wherein the one or more functional fluids selected from the following group of fluids: calibration solution, washing solution, reference liquid and reagent solution.

18. The method according to claim 1, wherein the physical usage parameter include information about at least one of: a temperature to which the disposable consumable has been ex-posed during operation of the analyzer, an air humidity of the disposable consumable, a temperature-dependent substance concentration, and a time-dependent concentration change.

19. The method according to claim 1, wherein the chemical usage parameter includes information about a usage-specific analyte content of the disposable consumable.

20. The method according to claim 1, wherein the characteristic data of the reference materials is target concentrations of substances contained in the reference materials.

21. The method according to claim 1, wherein the reference materials are organic reference substances such as glucose or urea which are degraded at an accelerated rate at elevated temperatures.

* * * * *